(12) United States Patent
Meeten

(10) Patent No.: US 6,330,826 B1
(45) Date of Patent: Dec. 18, 2001

(54) DYNAMIC SAG MONITOR FOR DRILLING FLUIDS

(75) Inventor: Gerald H. Meeten, Ware (GB)

(73) Assignee: Schlumberger Technology Corporation

( * ) Notice: Subject to any disclaimer, the term of this patent is extended or adjusted under 35 U.S.C. 154(b) by 0 days.

(21) Appl. No.: 09/499,988

(22) Filed: Feb. 8, 2000

(30) Foreign Application Priority Data

Feb. 15, 1999 (GB) .................................................. 9903205

(51) Int. Cl.[7] .............................. F04B 51/00; G01N 11/14
(52) U.S. Cl. ........................................ 73/152.62; 73/54.33
(58) Field of Search ................................ 73/53.02–64.56, 73/54.33, 152.01–152.62, 811, 843; 210/785; 405/130

(56) References Cited

U.S. PATENT DOCUMENTS

| 3,581,558 | * | 6/1971 | Porter et al. | ............................ 73/811 |
|---|---|---|---|---|
| 3,744,633 | * | 7/1973 | Schmidt, Jr. et al. | ................ 210/785 |
| 4,991,998 | * | 2/1991 | Kamino et al. | ....................... 405/130 |
| 5,103,679 | * | 4/1992 | Porter et al. | ............................. 73/843 |
| 5,777,212 | * | 7/1998 | Sekiguchi et al. | ................... 73/54.33 |

FOREIGN PATENT DOCUMENTS

| 0 417 885 A2 | | 6/1990 | (EP) . | |
|---|---|---|---|---|
| 2049521C | * | 12/1995 | (RU) | .............................. B01D/21/26 |

* cited by examiner

*Primary Examiner*—Hezron Williams
*Assistant Examiner*—Jay L. Politzer
(74) *Attorney, Agent, or Firm*—Thomas O. Mitchell

(57) ABSTRACT

An apparatus and a method are described for measuring the sag properties of a drilling fluid by using a conically or frustro-conically shaped inner body and an outer body having an opening with contours closely matching those of inner body such that in conjunction inner and outer body are separated by a narrow gap defining a conically or frustro-conically volume with a vertex; a motor drive for rotating the inner body with respect to the outer body; and a sampling access to determine the density of said drilling fluid within a localized part of said volume, wherein said sampling is permanently located in vicinity on said vertex.

17 Claims, 8 Drawing Sheets

DYNAMIC SAG MONITOR FOR DRILLING FLUIDS

This invention relates to an apparatus and a method for monitoring the sag of weight material in drilling fluids, particular for field testing at a drilling rig site.

BACKGROUND OF THE INVENTION

Hydrocarbons such as oil or gas are extracted from underground reservoirs through a well bored into the rock formation by means of a drill bit connected to a drill string or coil tubing. Rock cuttings are removed from near the bit by means of a drilling fluid or mud pumped down the pipe or coil tubing, which mud returns the cuttings to the surface via the annulus between drill string and the formation. In order to avoid wellbore instability the pressure of the mud at any depth should exceed the pressure of liquid in the pore space of the formation.

Commonly the mud is densified by the addition of a finely divided weighting agent, typically barite but often other minerals, the weighting agent being of density exceeding the unweighted mud density, and added in quantity judged to achieve the proper mud density. The lower limit of the particle size of the weighting agent is selected such that it does not affect the mud's rheology, neither damage the permeability of the formation in a reservoir section. An upper limit of the particle size is given by the mesh size of the shale shaker screens used to remove cuttings from the circulated mud. In practice the size lies in the 10 micron to 100 micron range. Being of this size the particles are not suspended by Brownian motion and so are prone to sediment under the influence of gravity; this process is termed "sag", or "barite sag".

A sag monitor as described herein measures the sedimentation of weight agents during downhole operations where the mud is neither circulated nor in a gelled state, e.g. during tripping, logging, or placing casing.

A device with similarity to that described herein was presented by Jefferson (ASME 91-PET-3, ASME Energy Sources Technol. Conf. & Exhibition, New Orleans, USA, Jan. 20–24, 1991). In his method the mud is sheared between the outside diameter of the rotor of Fann 35 Oilfield Rheometer, and the inside diameter of a Fann heat cup with a flat bottom. After shearing for a specified time, samples of mud are extracted from the top and bottom of the mud sample in the heat cup using a syringe inserted through the annulus at the top of the device. The density of the extracted samples was measured with either a pocket mud balance, or by weighing a known volume of extracted mud on a balance.

Among the disadvantages found in the known apparatus is a non-reproducible sampling technique. Furthermore, the apparatus tends to underestimate the sag. Also, the densest mud collects in a vertically heterogeneous layer at the base of the heat cup, and is not precisely sampled by the needle inserted from the top. Similarly there is a vertical gradient of mud density in the heat cup, leading to similar errors of density in the mud taken from the top of the heat cup.

The present invention addresses the above deficiencies in Jefferson's method, and further includes a method of real-time measurement of the sedimentation process.

SUMMARY OF THE INVENTION

The invention comprises of a conically or frustro-conically shaped inner body and an outer body having an opening with contours closely matching those of the inner body. In operation the inner body is suspended within the opening of the outer body leaving a gap which defines a conically or frustro-conically volume. Inner and outer body can perform a rotational movement with respect to each other, preferably by rotating the inner body (rotor) in the opening of the stationary outer body.

The cone angle is preferably close to 90 degrees.

Preferably the volume defined by the gap between inner and outer body is constant with respect to size and shape during rotation.

In a preferred embodiment, the inner body and the matching opening are extended by a cylindrically shaped part at one end, thereby increasing the volume of the gap between inner and outer body. In a preferred variant of this embodiment, the gap width is essentially constant in both the vertical and inclined parts of the gap. The width of the gap is preferably in the range of 1 to 3 mm.

The dimensions of the volume defined by the gap between inner and outer body and the operating conditions are preferably chosen such that, on rotation of the rotor, the mud contained in the intercylinder gap is subject to laminar shear, typically at rates between 1 to 60 $s^{-1}$. Simultaneously, it is advantageous to reduce the amount of mud necessary to make a measurement. Preferably the volume of the gap is less than 100 milliliter to facilitate the use of the sag monitor as field testing.

On sedimentation under shear the barite falls into the conical part of the gap and is focussed to the vertex. Hence mud at the vertex is strongly densified in a short time, typically 20 min. The barite (or other weighting agent) in the mud, in excess of that in the unsagged mud, is measured. This may be done via the mud density, or it may be done by other methods, e.g. from the mud's electrical or other properties. To measure the density directly, mud is extracted from the vertex with a small syringe whose entrance nozzle is as close as possible to the vertex. The mud volume extracted is limited to a fixed volume by the design of the syringe, and the mud density is obtained by weighing the full syringe.

It is feasible to extract the sample from the surface of the mud and determine the mud sag from the density of the lighter mud. However it is believed that such a measurement can be distorted by the development of bubbles in the sheared mud. The bubbles rise to the surface and make it difficult to achieve an accurate measurement of the sample's density.

The mud's electrical or other suitable properties may be measured via electrodes or sensors in the wall of the stator, so giving a continuous method of monitoring the sag. It is shown how a simple calibration may be obtained to derive the mud density from the electrical properties of the mud.

Although described in terms of a device for measuring the sedimentation of weighting agents in sheared drilling fluids, the same invention can be used for other particulate fluids used in the oilfield industry such as cement slurries or spacers, or for fluids where the particles are either denser (e.g. paints) or are less dense (e.g. oil-in-water emulsions) than the continuous or external phase.

These and other features of the invention, preferred embodiments and variants thereof, and further advantages of the invention will become appreciated and understood by those skilled in the art from the detailed description and drawings below.

MODE(S) FOR CARRYING OUT THE INVENTION

Figure 1:
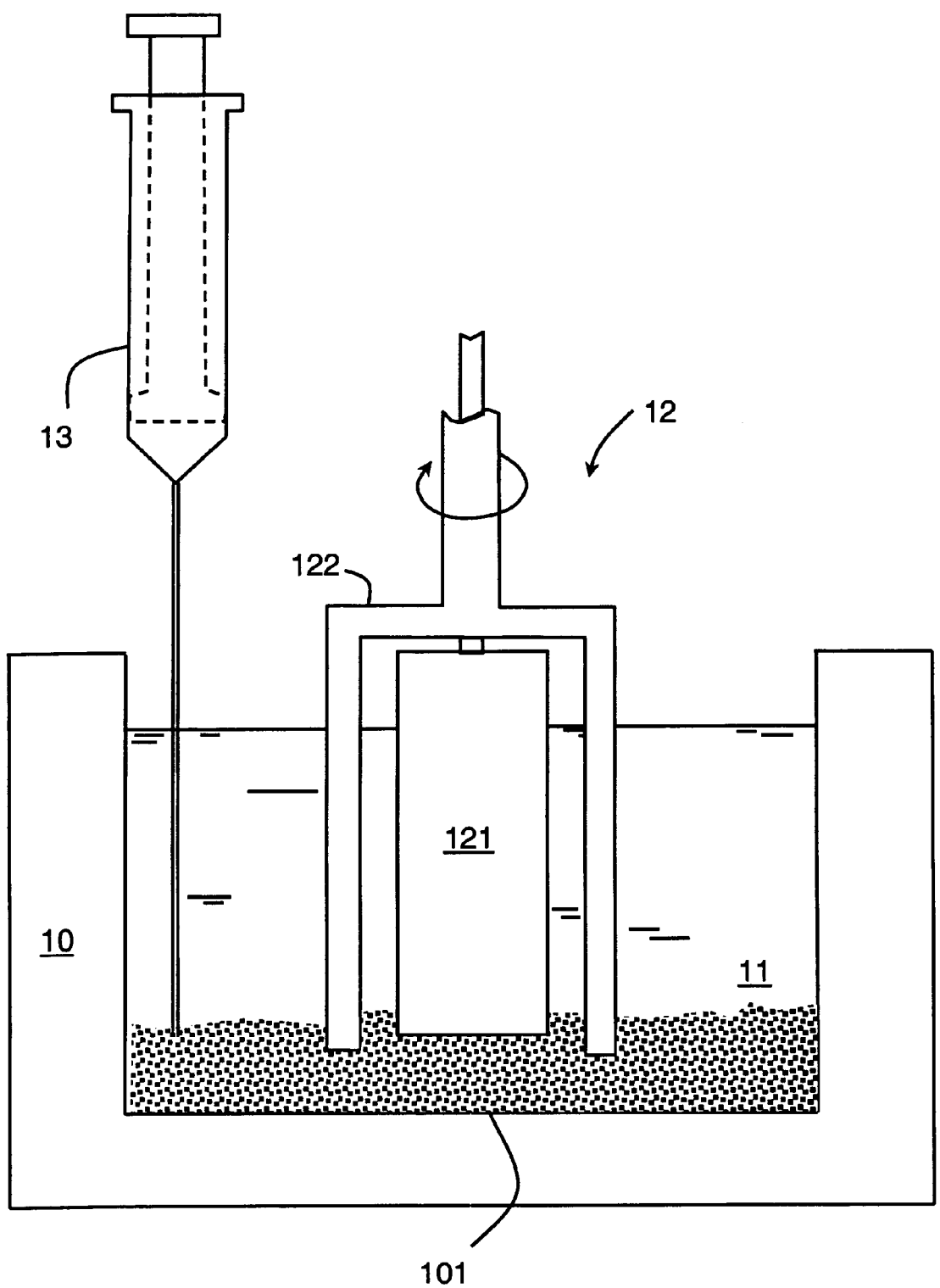
FIG. 1 is a schematic drawing illustrating a sag monitor as known in the prior art.

A prior art sag monitor as proposed by Jefferson is illustrated in FIG. 1. Its basic elements are a Fann heat cup 10 with a flat bottom 101. The cup is filled with mud 11, which is then sheared using a Fann 35 Oilfield Rheometer 12 (to API specification) comprising a static inner cylinder 121 (bob) and a rotating sleeve 122. The API Heat Cup (as used by Jefferson) has a inner diameter of ID=60.33 mm. The existing API rotor has OD=40.64 mm and ID=36.83 mm. The existing API bob (stator) 121 has OD=34.49 mm. These dimensions give a rotor-cup gap of 9.85 mm and a rotor-bob gap of 1.17 mm.

Following shear for a specified time, samples of mud are extracted from the top and bottom of the mud sample in the heat cup using a syringe 13 inserted through the annulus at the top of the device. The density of the extracted samples was measured with either a pocket mud balance, or by weighing a known volume of extracted mud on a balance. The rheometer rotational speed over the settling time was 100 RPM, which translates into a shear rate of approximately 170 s$^{-1}$ for the gap between rotor and bob. The rotor-bob gap is open, i.e., barite particles will fall from this 1.17 mm gap to the lowest part of the heat cup. Similarly, barite particles will fall also from the rotor-cup 9.85 mm gap into the lowest part of the heat cup. Thus the sample extracted by syringe in the method described by Jefferson will sample an uncontrolled mixture from the two regions. But for any given rotor speed, and because of the big difference between the gaps, the mud from which the particles fall has experienced a very different shear rate by a factor of about 9.85/1.17, i.e. about 8. Thus because the mixture from the two regions is uncontrolled, the shear rate pertaining to the extracted sample is undefined.

Moreover, the space between the (flat) bottom 101 of the heat cup and the lower end of the rotor 122 will also receive some ill-defined shear from the motion of the lower end of the rotor. For most muds, the shear is likely to be non-laminar in the rotor-cup gap (9.85 mm), and in the gap between the rotor's lower end and the bottom of the heat cup. Our studies (with a very well-defined shear rate everywhere accruing from the design of the new sag monitor) showed that non-laminar flow can act so as to reduce the barite sag, presumably owing to a re-mixing process, well-known to be a property of non-laminar flow. Thus it is possible that in Jefferson's method, barite sag may be high in the small (1.17 mm) gap, where the flow is certainly laminar and at a high shear rate, but small or negligible in the large (9.85 mm) gap where the shear is likely to be non-laminar, except for the very smallest rotor speeds where dynamic barite sag will be anyway small.

Figure 2:
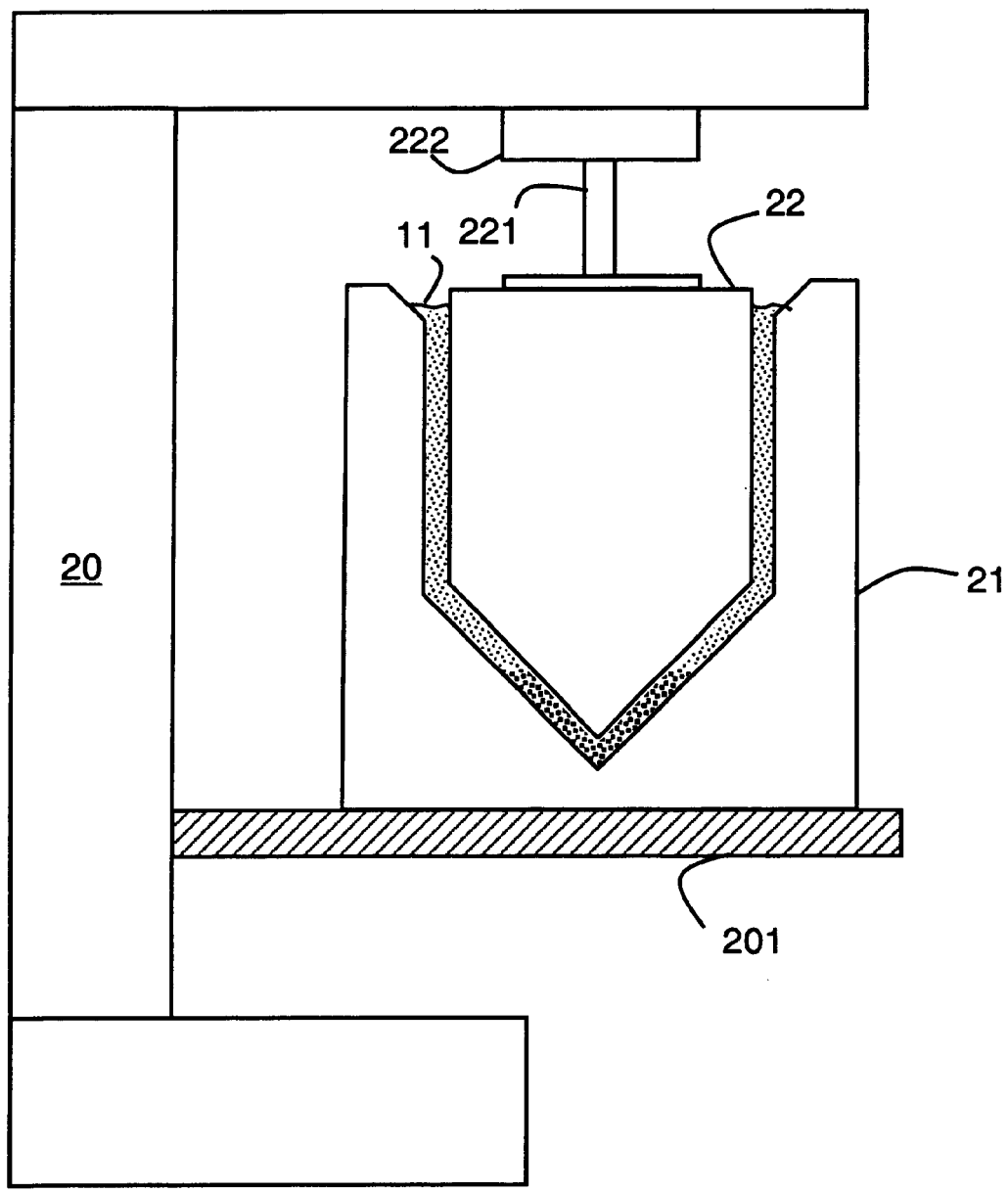
FIG. 2 is a schematic drawing illustrating a sag monitor according to the invention.

The present invention seeks to overcome the limitations of the prior art. FIG. 2 shows a schematic diagram of an example in accordance with the invention. A rigid frame 20 holds a vertically-adjustable table 201 which supports the conical-bottomed stator 21. The frame 20 also suspends the conical-ended rotor 22, coaxial with the stator 21, and which is rotated around the common axis at a known angular speed by shaft 221 driven by a motor 222 and appropriate gear drive attached to frame 20.

The intercylinder gap of 2.04 mm is filled with the mud 11 whose sag is to be measured. Following the period of shear set up by the relative motion of the rotor and stator, densified mud sediments to the lowest region of the intercylinder gap. The sag monitor is typically operated for less that one hour, but reasonably good results can be achieved with measurements of less than 30 minutes.

One measure of the dynamic sag is the excess density of the mud 11 over the original mud density prior to shear. Another measure of sag is the rate at which the density of the densified mud 11 increases with time. A suitable method or protocol is to shear the mud at a fixed shear rate γ.

For a Newtonian liquid between two cylinders the shear rate is given by $$\gamma(r) = \frac{\pi N a^2 b^2}{15(b^2 - a^2)r^2} \qquad (1)$$

where N is the rotor speed (in RPM), a is the rotor outer radius, b is the stator inner radius and r is the radial distance from the axis of the cylindrical rotor. A convenient measure of the shear rate is the geometric mean value γ given when r=√ab, i.e.

$$\gamma_{av} = \frac{\pi N a b}{15(b^2 - a^2)} \qquad (2)$$

For given dimensions a and b the geometric mean shear rate is thus given by $\gamma_{av}=kN$ where the magnitude of k is typically 1 s$^{-1}$/RPM. Typically, a shear rate of 10 to 30 s$^{-1}$ over a time period of 15 to 60 min has been found to be suitable for a range of muds.

In theory it is well known that the shear rate above can be maintained in the conical part of the gap only if the gap decreases linearly with radial distance as the vertex is approached. This was investigated by measuring the excess density of the same mud for different rotors and stators having the same vertical gap width, but having different gap width tapers in the conical section. It was found that a tapered gap or a uniform gap in the conical section gave practically identical results. Thus the preferred design has a uniform gap in the vertical and conical sections of the intercylinder gap. This allowed for a greater volume of the densified mud, which increased the measurement precision, and also avoided interference between the rotor and stator caused by bridges of larger weighting particles.

The mud densification caused by the dynamic sag can be measured by extracting a small sample of the densified mud 11 and measuring its density, or the density may be obtained by a non-extractive method.

The former method gives the density directly, which parameter is of the most direct importance to mud engineering, but this method of measurement allows only one data point per run. The latter method gives continuously the densified mud density during shear. Both methods are described below.

Figure 3:
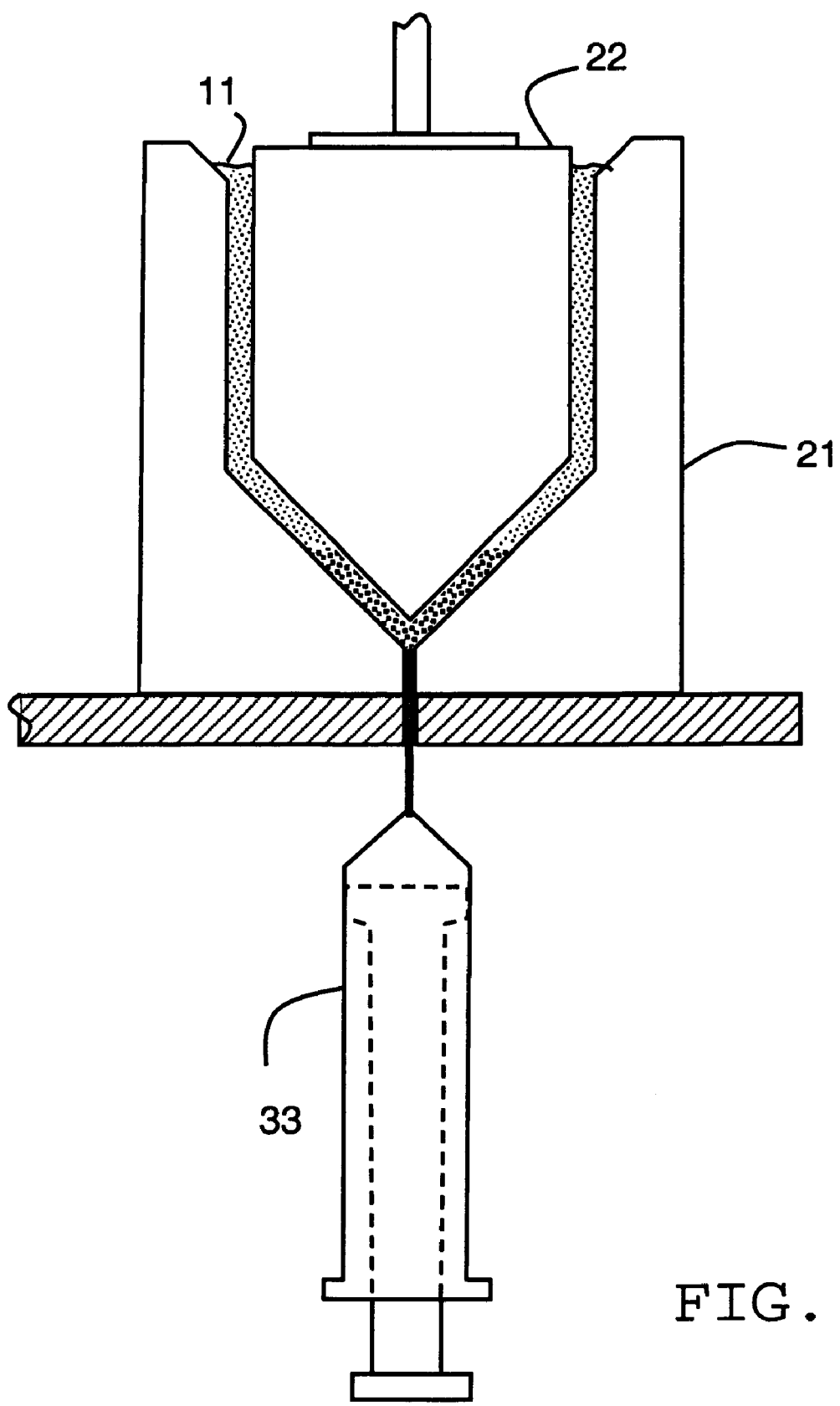
FIGS. 3,4 show variants of the sag monitor.
Figure 4:
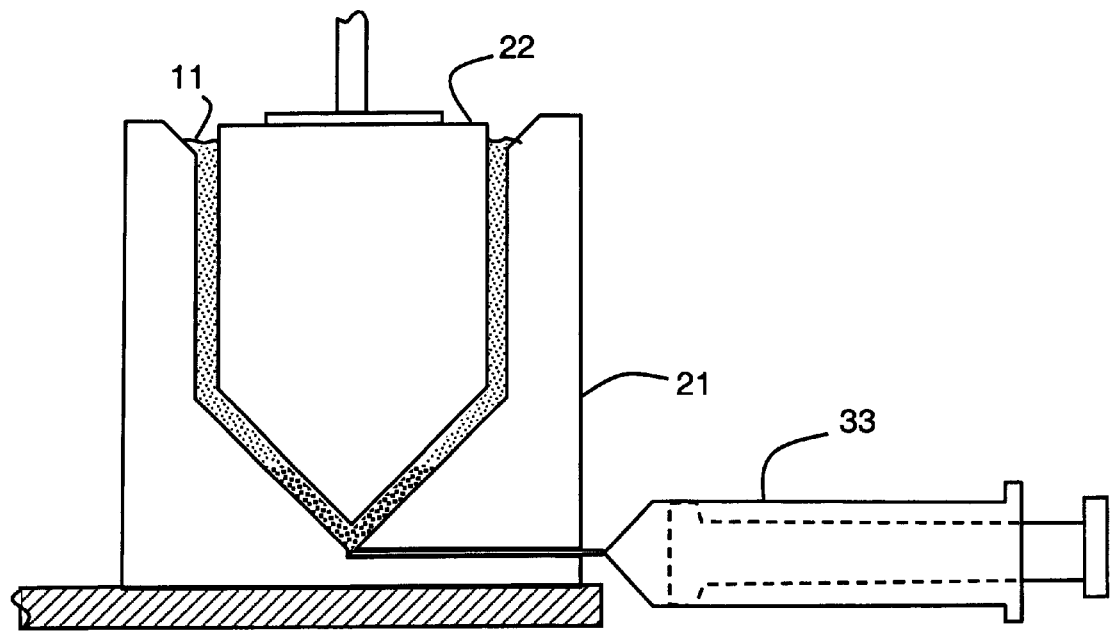

In an extractive use, the extracted sample must be of substantially less volume than that of the total mud volume contained in the intercylinder gap, or no change in density will be observed. An extractive volume of about 10% of the total volume was found preferable. This volume was extracted using a syringe 33 having a nominal volume of 2 milliliter, as shown in FIG. 3 and FIG. 4. It was found preferable to use a syringe which exerted a stop on the piston's outward motion, so that the extractive syringe volume was well-defined. The extractive syringe volume was obtained gravimetrically using a fluid such as water with a known density, and the mud density in the extractive volume was similarly obtained. It is preferable to minimise the volume of unsheared mud at the vertex of the cones, and to this end the syringe nozzle is placed as close as possible to the vertex of the stator's conical vertex.

FIG. 3 shows an example of the invention in which the syringe's cylindrical axis is coaxial with the common cylindrical axes of the rotor 22 and the stator 21. This coaxiality confers a symmetrical sampling of densified mud when the syringe piston is pulled down.

An alternative arrangement is shown in FIG. 4, in which the syringe's cylindrical axis is horizontal. Tests comparing the configurations of FIG. 3 and FIG. 4 showed little difference between their performance.

Figure 5:
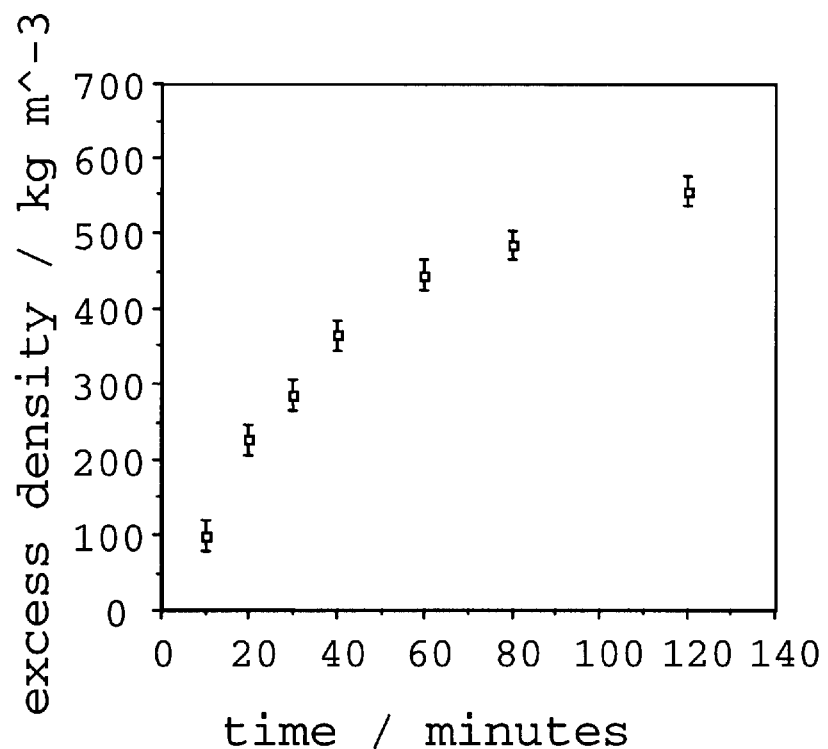
FIG. 5 shows the increase with time of the excess density of a KCl/polymer mud sheared at a rate of 30 s$^{-1}$.
Figure 6:
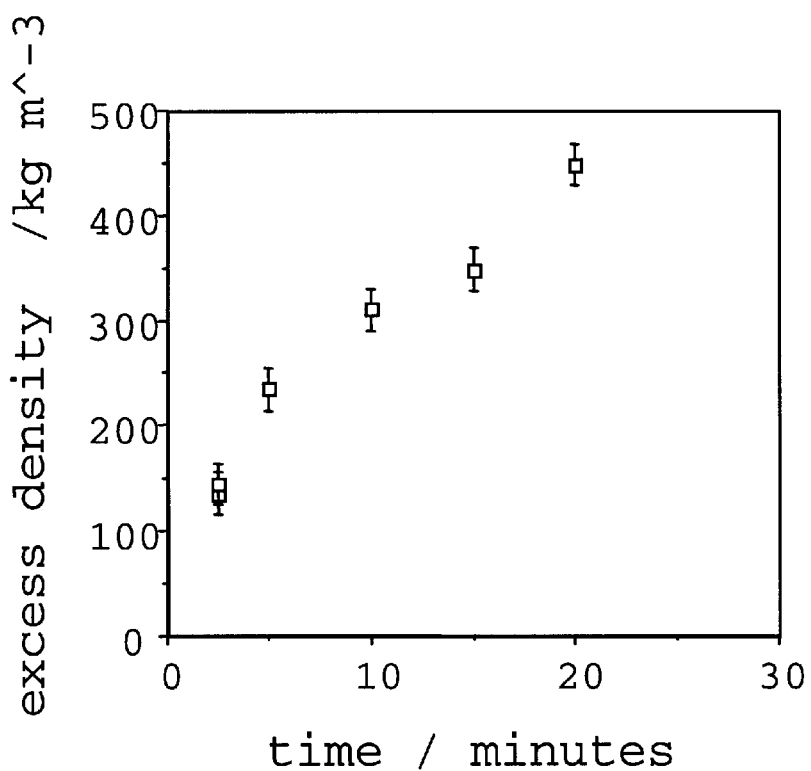
FIG. 6 shows the increase with time of the excess density of a waterbase bentonite mud sheared at a rate of 5 s$^{-1}$.
Figure 7:
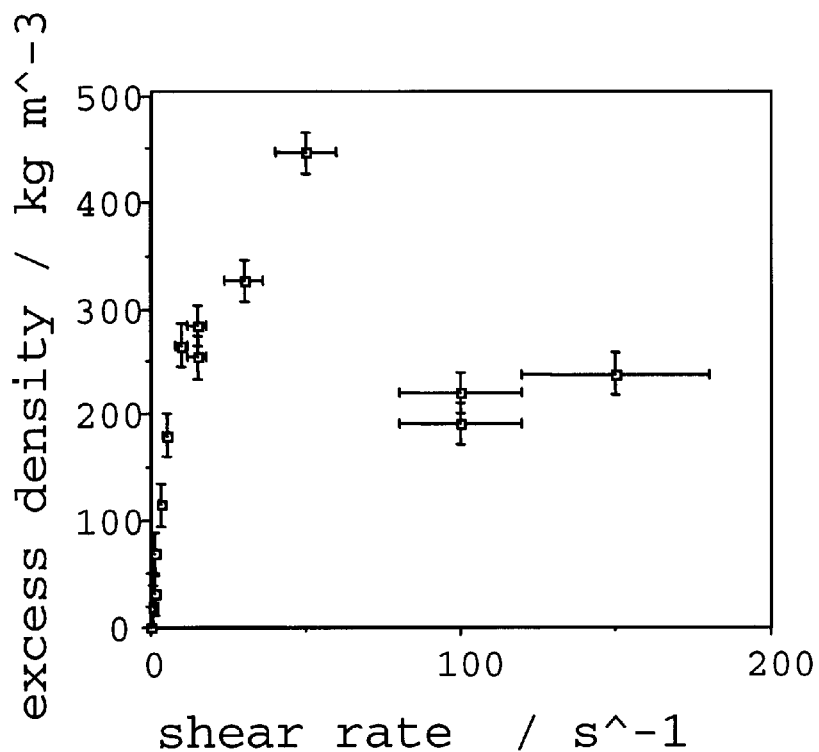
FIG. 7 shows the increase with shear rate of the excess density of a KCl/polymer mud sheared for a duration 30 min.
Figure 8:
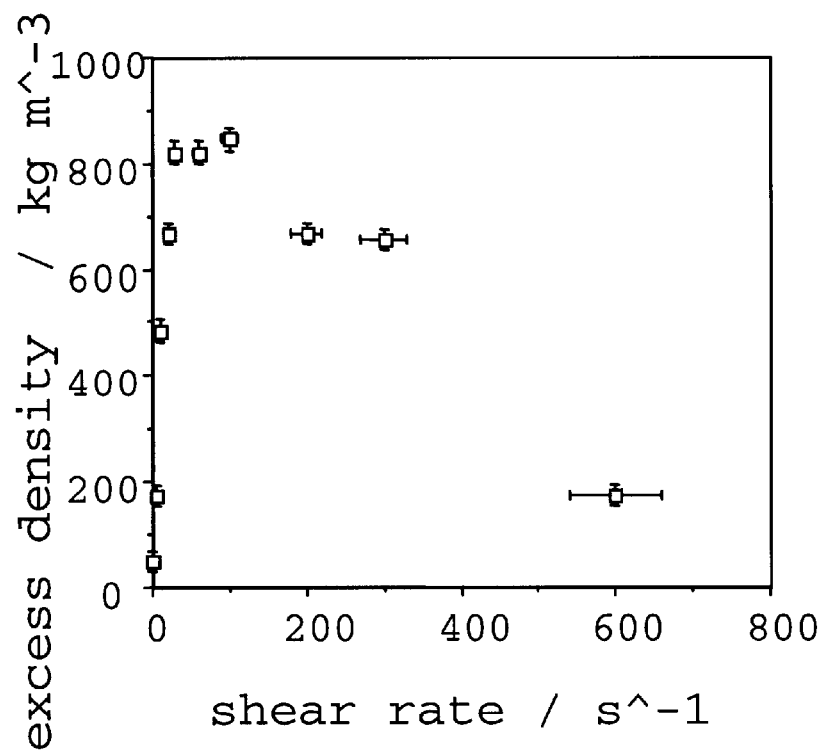
FIG. 8 shows the increase with shear rate of the excess density of a waterbase bentonite mud sheared for a duration 30 min.
Figure 9:
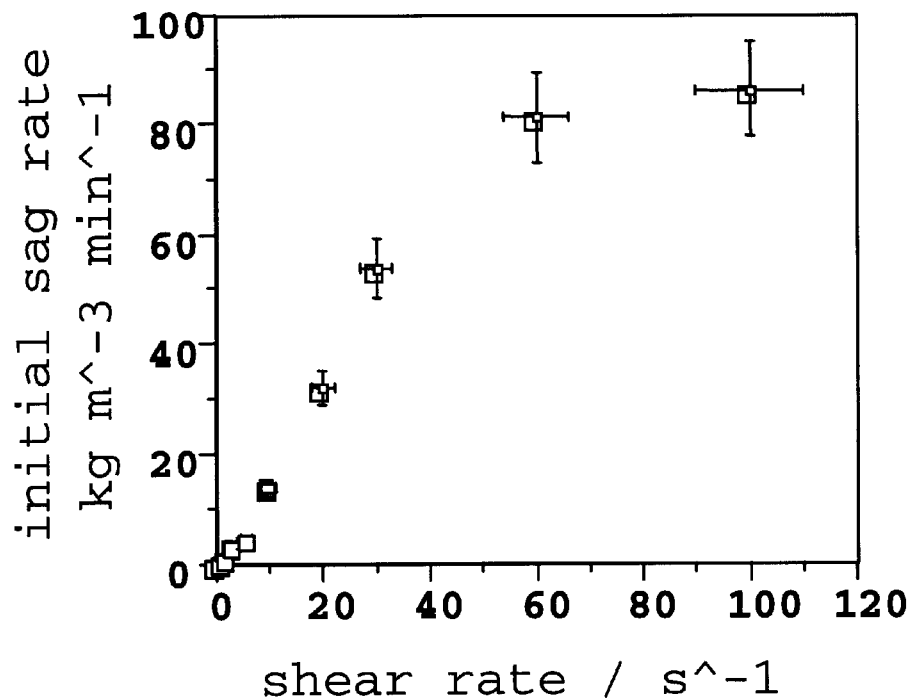
FIG. 9 shows the gradient of the excess density plotted versus the shear rate for a waterbase bentonite mud.
Figure 10:
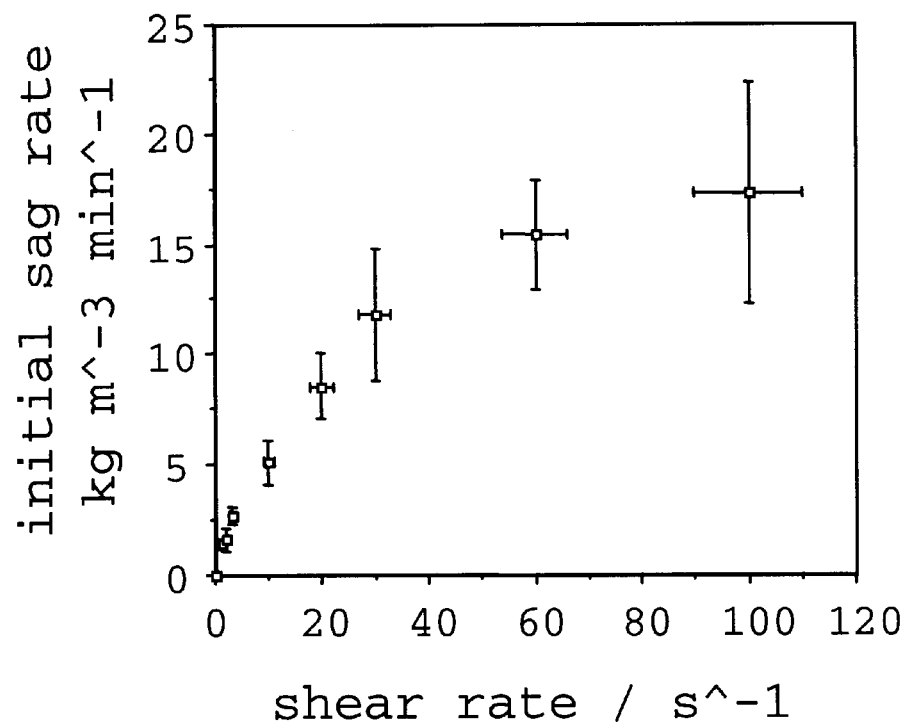
FIG. 10 shows the plot of FIG. 9 for a KCl/polymer mud.

FIGS. 5 to 10 inclusive show results typical of the described invention, all measured with drilling muds of original density made up with barite to be about 1500 kg m$^{-3}$. FIG. 5 shows the increase with time of the excess density of a KCl/polymer mud sheared at a rate of 30 s$^{-1}$. The plateau after about 2 hr is expected when there is little remaining barite in suspension. FIG. 6 shows the increase with time of the excess density of a waterbase bentonite mud sheared at a rate of 5 s$^{-1}$. FIG. 7 shows the increase with shear rate of the excess density of a KCl/polymer mud sheared for a duration 30 min. This shows the ability of the invention to measure the sag in laminar shear, up to about 50 s$^{-1}$, and also in non-laminar shear above 50 s$^{-1}$. The decrease of the excess density in non-laminar shear is owing to upward convection arising from the Taylor vortices. FIG. 8 shows the increase with shear rate of the excess density of a waterbase bentonite mud sheared for a duration 30 min, and shows a similar behaviour to the KCl/polymer mud in FIG. 7. A measure of the sag is provided by the sag rate at small times, e.g. the gradients of the early-time data of FIGS. 5 and 6. FIG. 9 shows this rate plotted versus the shear rate for a waterbase bentonite mud, and FIG. 10 shows the same plot for a KCl/polymer mud.

The invention described is not limited to the syringe method of extraction and density analysis. In another extractive method the extracted sample is analysed for a property related to the sag, such as density, weighting agent concentration, particle size, etc. For example the density of the extracted sample can be analysed by an inertial rather than gravimetric method, e.g. by a vibrating U-tube densitometer. Alternatively the weighting agent concentration can be measured by a method which measures e.g. the electrical properties, ultrasonic properties, gamma-ray or X-ray absorption or fluorescence.

Figure 11:
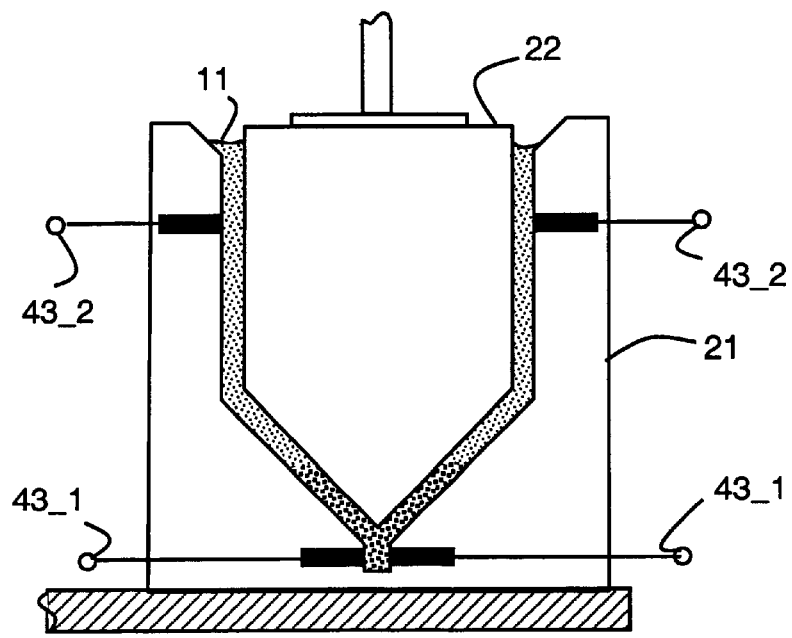
FIG. 11 shows a variant of the invention suitable for continuous monitoring.

The invention described is not limited to the extractive method of density analysis, but permits measurement of properties related to sag in real time. For example the densified mud at the vertex of the stator cone can be continuously monitored with time from the beginning of shear by means of an appropriate sensor placed at the vertex. As above, this sensor could measure e.g. electrical properties (conductivity, permittivity), ultrasonic properties (velocity, attenuation, impedance), gamma-ray or X-ray absorption or fluorescence. The electrical properties of the small volume of densified mud available for analysis at the vertex are readily measured by a pair of electrodes 43_1 positioned close to the vertex as shown in FIG. 11. The lightening of the mud in the vertical part of the intercylinder gap may also be similarly measured using electrodes 43_2 as shown in FIG. 11.

An advantage of the electrical method is that the impedance $Z_{12}$ between electrodes 43_1 may be compared in an analogue manner with the impedance $Z_{34}$ between electrodes 43_2, by means of well known methods such as variants on the Wheatstone Bridge principle. The electrodes can be connected to a suitable device (not shown) for measuring the electrical impedance ratio $Z_{12}/Z_{34}$. As the mud sags, $Z_{12}$ will generally change in an opposite direction to $Z_{34}$, hence increasing the sensitivity of the invention to the sag, and so minimising the time spent in measuring it.

An example of the electrical continuous method is given as follows, in which the property measured is the electrical conductance. This is suitable for water-based muds, in which the weighting agent is either non-conducting, or is appreciably less conducting than the interstitial liquid phase, i.e. water containing dissolved ions. This example makes use of the theory of non-conducting spherical particles in a conducting fluid, known as such. This theory teaches that the mud's conductivity $\sigma_{mud}$ is given by $$\sigma_{mud}=\sigma_{liq}(1-v_{bar})^{3/2} \qquad (3)$$

where $\sigma_{liq}$ refers to the conductivity of the unweighted mud, and $v_{bar}$ is the volume fraction of the barite or the weighting agent. The density of the mud is given by $$\rho_{mud}=(1-v_{bar})(\rho_{liq}-\rho_{bar})+\rho_{bar} \qquad (4)$$

where $\rho_{bar}$ is the granular density of the weighting agent. On eliminating $v_{bar}$ from Equations (3) and (4) it follows that $$\rho_{mud} = \left(\frac{\sigma_{mud}}{\sigma_{liq}}\right)^{2/3}(\rho_{liq}-\rho_{bar})+\rho_{bar}. \qquad (5)$$

Figure 12:
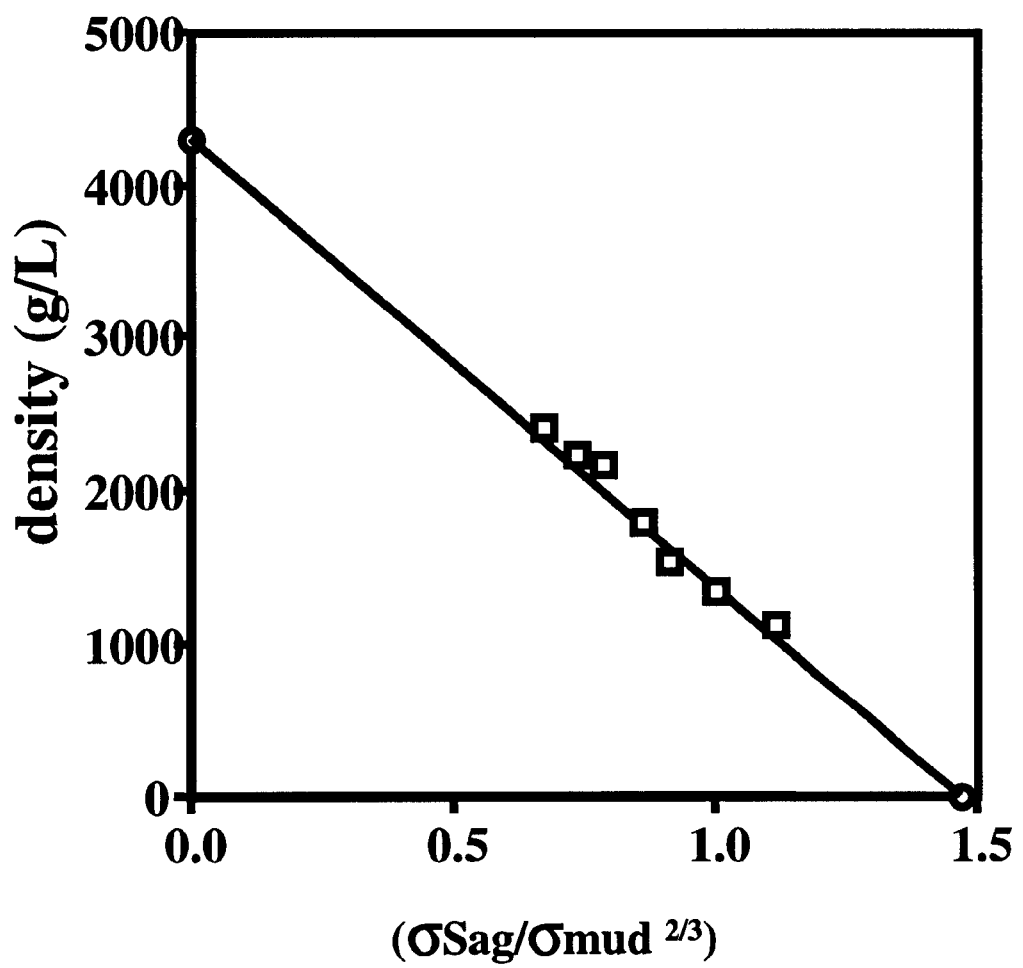
FIG. 12 shows a plot of the conductivity vs mud density.

A similar relation may be deduced between the density $\rho_{sag}$ of the sagged mud and its conductivity $\sigma_{sag}$, i.e.

$$\rho_{sag} = \left(\frac{\sigma_{sag}}{\sigma_{liq}}\right)^{2/3}(\rho_{liq}-\rho_{bar})+\rho_{bar} \qquad (6)$$

and eliminating $\sigma_{liq}$ from Equations (5) and (6) gives $$\rho_{sag} = \left(\frac{\sigma_{sag}}{\sigma_{mud}}\right)^{2/3}(\rho_{mud}-\rho_{bar})+\rho_{bar} \qquad (7)$$

which relation provides the desired connection between the density $\rho_{sag}$ of the sagged mud and its conductivity. Equation (7) shows that $\rho_{sag}=\rho_{bar}$ when $\sigma_{sag}/\sigma_{mud}=0$, and also that $\rho_{sag}=0$ when $(\sigma_{sag}/\sigma_{mud})^{2/3}=\rho_{bar}/(\rho_{bar}-\rho_{mud})$. The quantities $\rho_{bar}$ and $\rho_{bar}/(\rho_{bar}-\rho_{mud})$ are accurately known so that for any particular mud a linear graph may be constructed such as the graph shown in FIG. 12, in which graph the point $\sigma_{sag}/\sigma_{mud}=0$, $\rho_{sag}=\rho_{bar}$ is connected by a straight line to the point $(\sigma_{sag}/\sigma_{mud})^{2/3}=\rho_{bar}/(\rho_{bar}-\rho_{mud})$, $\rho_{sag}=0$. The data points (squares) in FIG. 12 show experimental $\rho_{sag}$ and $\sigma_{sag}$ data, appropriately plotted. The good fit between these points and the theoretical straight line validates Equation (7) and shows that a calibration graph to relate the density of the sagged mud to its electrical conductivity can be obtained without making electrical calibration measurements on the mud whose sag is to be investigated.

For highly non-spherical particles it is possible that Equation (3) is invalid. For this case the above procedure may be used to measure the sagged mud density from the sagged mud conductivity, but by using a relation between the density $\rho_{sag}$ and the conductivity $\sigma_{sag}$ of the sagged mud, obtained via experiment.

What is claimed is:

1. An apparatus for measuring the sag properties of a drilling fluid comprising:

a conically or frustro-conically shaped inner body and an outer body having an opening, said opening having a contour closely matching the contour of the inner body such that, in conjunction, inner and outer body are separated by a narrow gap defining a conically or frustro-conically shaped volume with a vertex at one end;

a motor drive adapted to exert a shear force on fluid in said volume; and a sampling point, permanently located in the vicinity of said vertex, for extracting a sample of mud of said gap and to determine sedimentation of said drilling fluid within a localized part of said volume.

2. The apparatus of claim 1, wherein the shear force for is generated by a relative rotational movement of the inner body and outer body.

3. The apparatus of claim 1, wherein the sampling point comprises a sensor to determine the sedimentation.

4. The apparatus of claim 1, wherein the sampling point comprises a bore through the outer body.

5. The apparatus of claim 1, wherein the gap width is selected such that the apparatus can be operated under laminar mud shear conditions.

6. The apparatus of claim 1, wherein the gap width between inner and outer body is essentially uniform.

7. The apparatus of claim 1, wherein gap width between inner and outer body is essentially uniform and less than 5 mm.

8. The apparatus of claim 1, wherein the gap width between inner and outer body is essentially uniform and in the range of 1 to 3 mm.

9. The apparatus of claim 1, wherein the inner body comprises a cylindrically shaped extension and the opening in the outer body comprises a matching extension so as to increase the volume defined by the gap between inner and outer body.

10. The apparatus of claim 9, wherein the volume defined by the gap between inner and outer body is less than 50 milliliter.

11. A method of monitoring the sag of a drilling fluid, said method comprising the steps of:

lowering a conically or frustro-conically shaped inner body into an outer body having an opening with a contour closely matching the contour of inner body such that, in conjunction, inner and outer body are separated by a narrow gap defining a conically or frustro-conically volume with a vertex at one end;

filling said volume with said drilling fluid;

generating a shear across said gap; and sampling said drilling fluid within a localized part of said volume to determine its sedimentation, wherein said sampling is performed at a stationary location within the vicinity of said vertex.

12. The method of claim 11, wherein the shear within the volume is laminar.

13. The method of claim 11, wherein the shear rate within the volume is selected from a range of 6 to 60 $s^{-1}$.

14. The method of claim 11, wherein the drilling fluid is sampled by extracting a sample through a bore in the outer body leading to a location close to the vertex.

15. The method of claim 14, further including the step of determining the density of the sample.

16. The method of claim 11, wherein the drilling fluid is sampled by placing a sensor sensitive to the sedimention at a location close to the vertex.

17. The method of claim 11, wherein the drilling fluid is sampled by placing a sensor sensitive to the sedimention at a location close to the vertex and the sedimentation is monitored while shearing said drilling fluid.

* * * * *